(12) United States Patent
Su et al.

(10) Patent No.: US 10,987,288 B2
(45) Date of Patent: Apr. 27, 2021

(54) DEEP-SEA WATER CONCENTRATE SKIN APPLICATION KIT AND USE THEREOF

(71) Applicants: Yin-Ming Lo, New Taipei (TW); Jane-Yi Su, New Taipei (TW)

(72) Inventors: Jane-Yi Su, New Taipei (TW); Miao-Yun Chiang, New Taipei (TW); Chia-Yun Chang, New Taipei (TW)

(73) Assignees: Yin-Ming Lo, New Taipei (TW); Jane-Yi Su, New Taipei (TW)

( * ) Notice: Subject to any disclaimer, the term of this patent is extended or adjusted under 35 U.S.C. 154(b) by 0 days.

(21) Appl. No.: 16/213,132

(22) Filed: Dec. 7, 2018

(65) Prior Publication Data

US 2019/0175460 A1    Jun. 13, 2019

(30) Foreign Application Priority Data

Dec. 8, 2017   (TW) .................................. 106143216
Aug. 10, 2018   (TW) .................................. 107128064

(51) Int. Cl.

| | |
|---|---|
| *A61K 8/19* | (2006.01) |
| *A61Q 19/02* | (2006.01) |
| *A61K 8/04* | (2006.01) |
| *A61K 9/06* | (2006.01) |
| *A61Q 19/08* | (2006.01) |
| *A61P 17/02* | (2006.01) |
| *A61K 33/00* | (2006.01) |

(52) U.S. Cl.
CPC ................ *A61K 8/19* (2013.01); *A61K 8/042* (2013.01); *A61K 9/06* (2013.01); *A61K 33/00* (2013.01); *A61P 17/02* (2018.01); *A61Q 19/02* (2013.01); *A61Q 19/08* (2013.01)

(58) Field of Classification Search
CPC combination set(s) only.
See application file for complete search history.

(56) References Cited

U.S. PATENT DOCUMENTS 8,354,099 B2 *   1/2013   Maor ..................... A61K 8/965
                                                                            424/45
2016/0213757 A1 *   7/2016   Edelson ............... A61K 9/1075

\* cited by examiner

*Primary Examiner* — Celeste A Roney
(74) *Attorney, Agent, or Firm* — Muncy, Geissler, Olds & Lowe, P.C.

(57) ABSTRACT

A deep-sea water concentrate skin application kit of deep-sea active concentrate and skincare formula is provided. The deep-sea water concentrate skin application kit has the following properties of micronizing the skincare formulas immediately, and decreasing the surface tension of the deep-sea active concentrate immediately; furthermore, the deep-sea active concentrate can become a driving force for the permeability of the micronized skincare formulas. Therefore, the deep-sea water concentrate skin application kit can be more easily absorbed into the skin (dermis). A manufacturing method of the deep-sea water concentrate skin application kit is also provided to improve skin appearance.

5 Claims, 26 Drawing Sheets

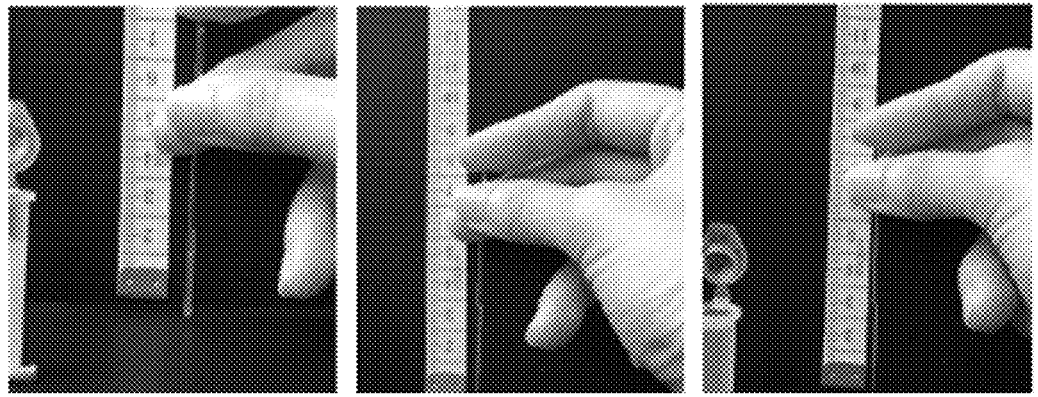

Deep-sea water concentrate with 0% concentration height of capillary tube: 1 cm

Deep-sea water concentrate with 50% concentration height of capillary tube: 3 cm Deep-sea water concentrate with 10% concentration height of capillary tube: 3 cm

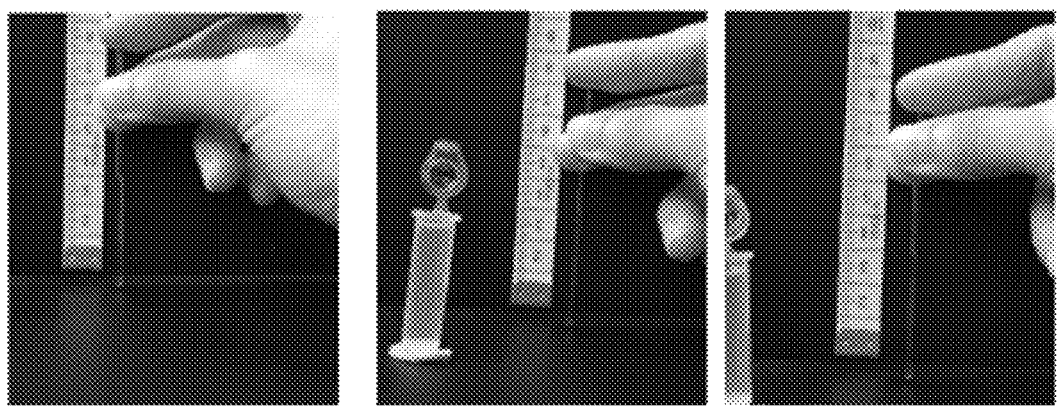

Deep-sea water concentrate with 5% concentration height of capillary tube: 3 cm

Deep-sea water concentrate with 2.5% concentration height of capillary tube: 3 cm Deep-sea water concentrate with 1.25% concentration height of capillary tube: 3 cm

FIG. 3B

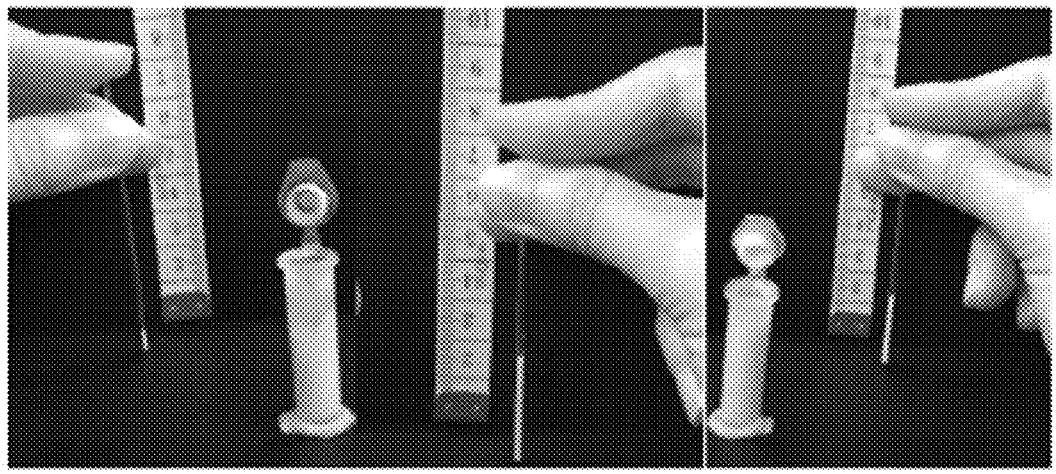

| Deep-sea water concentrate with 0% concentration height of capillary tube: 0.5 cm | Deep-sea water concentrate with 50% concentration height of capillary tube: 2 cm | Deep-sea water concentrate with 10% concentration height of capillary tube: 2 cm |

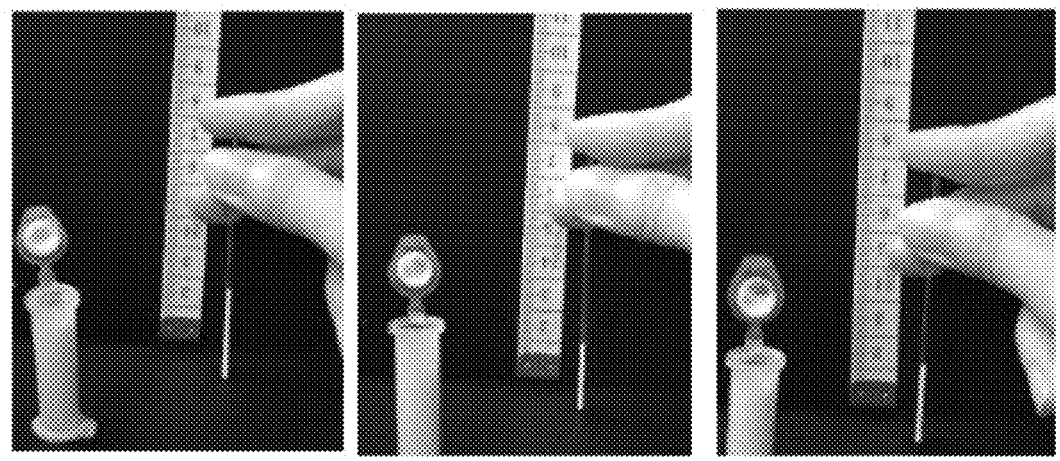

| Deep-sea water concentrate with 5% concentration height of capillary tube: 2 cm | Deep-sea water concentrate with 2.5% concentration height of capillary tube: 1.5 cm | Deep-sea water concentrate with 1.25% concentration height of capillary tube: 1.5 cm |

FIG. 3C ly Patent Application No. 106143216, filed on Dec. 8, 2017 and No. 107128064, filed on Aug. 10, 2018, in the Taiwan Intellectual Property Office, the disclosure of which is incorporated herein in its entirety by reference.

BACKGROUND OF THE INVENTION

1. Field of the Invention

The present invention relates to a deep-sea water concentrate skin application set of deep-sea water concentrate and skincare formulas, more particularly to a composition of deep-sea water concentrate and a skincare formulas manufactured timely, and micronized molecular groups which can reduce surface tension of deep-sea water concentrate, and the high concentration of ionic minerals can become driving force for permeability, so that skin cells can absorb the skincare formulas more easily.

2. Description of the Related Art

Deep-sea water is low-temperature, clean and pollution-free seawater gathered from below 200 meters under sea level. This deep-sea water is rich in mineral ions, such as magnesium, calcium and potassium, and nutrients, and inorganic components having high solubility and low decomposability. The deep-sea water is also rich in minerals mainly because sunlight cannot reach the deep sea and photosynthesis cannot occur, and inorganic nutrient salts are not consumed by phytoplankton. Therefore, compared with surface-sea water, the deep-sea water has a higher content of inorganic nutrient salts. The deep-sea water is currently widely used in health drinks, food, v products, and aquaculture because of rich inorganic nutrient salts thereof.

In recent years, deep-sea water has been widely used in food processing, agriculture, and medicinal applications. Research papers have pointed out that deep-sea water can not only reduce blood fat, lipid oxidation, vascular sclerosis, and hypertension, but also reduce the proliferation of vascular walls. In the study of atopic dermatitis, it is also found that patient drinking or soaking in deep-sea water can have improvement in the symptoms of skin inflammation and allergies; however, the deep-sea water has not been applied to the cosmetics industry on a large scale. In addition, drinking deep-sea water has also been found to have the benefit of improving cataracts.

The deep-sea water can be collected only in four places around the world, and a Taiwan company has successfully collected deep-sea water to make a concentrate, which can be eaten and used as a skincare product. It has been pointed out in the literature that deep-sea water can stimulate collagen to regenerate, whiten skin, inhibit or treat inflammation. However, deep-sea water has not been widely used in the addition of cosmetic products. Generally, commercially available skincare products require an emulsifier to stably fuse oil and water, so that the molecular groups thereof are large and not easily absorbed by skin, while the deep-sea water concentrate has a balanced and stable ion composition, which is a state in which cells are easily absorbed. However, the property of high surface tension of the deep-sea water makes it difficult to permeate into the skin. There is still no literature disclosing effective products of directly mixing the deep-sea water concentrate liquid and the skincare product. In order to provide more effective skincare products and increase the industrial value of deep-sea water, there is an urgent need to provide a composition containing deep-sea water concentration (liquid/powder) and skincare formula.

SUMMARY OF THE INVENTION

In order to solve the above-mentioned problems, the present invention provides a skincare application kit of the deep-sea water concentrate and skincare formulas, and the skincare application kit can improve the health or the appearance of skin. The present invention also provides a use of the skincare application kit and a manufacturing method of the skincare application kit. The deep-sea water concentrate skin application set of the present invention is characterized that the skincare formula can be micronized immediately to decrease surface tension of the deep-sea water concentrate, so as to solve the problem that the skin is not easy to absorb the deep-sea water concentrate. Furthermore, the properties of the deep-sea water concentrate can become a driving force for permeability of micronized skincare formula so that skin (dermis) can absorb more easily.

According to an embodiment, the present invention provides a deep-sea water concentrate skin application set including a first agent and a second agent. The first agent is deep-sea water concentrate, and the second agent is skincare formula. The first agent and the second agent are packaged independently.

Preferably, the present invention provides a deep-sea water concentrate skin application set, wherein a concentration of magnesium of the deep-sea water concentrate is in a range from 6,500 mg/l to 110,000 mg/l.

Preferably, the present invention provides a deep-sea water concentrate skin application set, wherein a concentration of sodium of the deep-sea water concentrate is in a range from 3,800 mg/l to 30,000 mg/l, a concentration of potassium is in a range from 400 mg/l to 18,000 mg/l, and a concentration of calcium is in a range from 100 mg/l to 500 mg/l.

Preferably, the present invention provides a deep-sea water concentrate skin application set, wherein the concentration of the deep-sea water concentrate is in a range from 80,000 mg/l to 420,000 mg/l, and the salinity of the deep-sea water concentrate is in a range from 380‰ to 430‰.

Preferably, the present invention provides a deep-sea water concentrate skin application set, wherein each 100 g of the deep-sea water concentrate contains calcium in a range from 1000 mg to 1500 mg, magnesium in a range from 1,400 mg to 2,100 mg, sodium in a range from 2,000 mg to 4,000 mg, potassium in a range from 1,400 mg to 2,100 mg, sulfate lower than 6.5 wt %, and a solution of sea minerals with a density in a range from 1.17 $g/cm^3$ to 1.32 $g/cm^3$.

Preferably, the present invention provides a deep-sea water concentrate skin application set, wherein the deep-sea water concentrate is obtained from 200 m under the surface of the sea.

Preferably, the present invention provides a deep-sea water concentrate skin application set, wherein the deep-sea water concentrate is obtained from 500 m under the surface of the sea.

Preferably, the present invention provides a deep-sea water concentrate skin application set, wherein the skincare formula is whiting product, moisturizer product, anti-wrinkle product, wound healing product, medicine or beauty treatment product, collagen proliferation promoting product, and product for improving skin appearance.

Preferably, the present invention provides a deep-sea water concentrate skin application set, wherein the deep-sea water concentrate is liquid or powder.

Preferably, the present invention provides a deep-sea water concentrate skin application set, wherein the skincare formulas are gelatinous or creamy.

According to an embodiment, the present invention provides a method of improving permeability of a skincare formula, and the method includes the following steps: (a) a skincare formula is provided; (b) the skincare formula and a deep-sea water concentrate are mixed before use; and the method is characterized in micronizing the skincare formula immediately to improve the permeability of the skincare formula, so that the skincare formula can quickly permeate into the skin to the dermis.

Preferably, the present invention provides a method of improving permeability of a skincare formula, wherein a concentration of magnesium of the deep-sea water concentrate is in a range from 6,500 mg/l to 110,000 mg/l.

Preferably, the present invention provides a method of improving permeability of a skincare formula, wherein a concentration of sodium of the deep-sea water concentrate is in a range from 3,800 mg/l to 30,000 mg/l, a concentration of potassium is in a range from 400 mg/l to 18,000 mg/l, and a concentration of calcium is in a range from 100 mg/l to 500 mg/l.

Preferably, the present invention provides a method of improving permeability of a skincare formula, wherein a concentration of the deep-sea water concentrate is in a range from 80,000 mg/l to 420,000 mg/l, and the salinity of the deep-sea water concentrate is in a range from 380‰ to 430‰.

Preferably, the present invention provides a method of improving permeability of a skincare formula, and the deep-sea water concentrate is liquid or powder.

Preferably, the present invention provides a method of improving permeability of a skincare formula, and the skincare formula is gelatinous or creamy.

Preferably, the present invention provides a method of improving permeability of a skincare formula, and after the deep-sea water concentrate is mixed with the skincare formula, an effective concentration of the deep-sea water concentrate is at least higher than or equal to 1.25 (v/v) %.

Preferably, the present invention provides a method of improving permeability of a skincare formula, and after the deep-sea water concentrate and the skincare formula are mixed, the mixture is applied to an affected part.

Preferably, the present invention provides a method of improving permeability of a skincare formula, wherein the affected part is the skin.

According to an embodiment, the present invention provides a method of caring skin, and the method includes steps of immediately applying a deep-sea water concentrate skin application set of claim 1 to a skin after the deep-sea water concentrate skin application set of claim 1 is manufactured.

Preferably, the present invention provides a method of caring skin, wherein after the deep-sea water concentrate is mixed with the skincare formula, the effective concentration of the deep-sea water concentrate is at least higher than or equal to 1.25 (v/v) %.

Preferably, the present invention provides a method of caring skin, wherein the deep-sea water concentrate skin application set can quickly permeate into the skin to reach the dermis, thereby achieving effect of anti-wrinkle, whiting, and firming, for improving skin appearance.

BRIEF DESCRIPTION OF THE DRAWINGS

The structure, operating principle and effects of the present invention will be described in detail by way of various embodiments which are illustrated in the accompanying drawings.

FIG. 1A is a picture showing the wound before the deep-sea water concentrate skin application set is applied to the wound. FIG. 1B is a picture showing the wound just being applied with the deep-sea water concentrate skin application set. FIG. 1C is a picture showing the wound applied with the deep-sea water concentrate skin application set several hours ago.

FIGS. 3A to 3C show the changes of physical properties of the mixture of the deep-sea water concentrate liquid and the skincare formulas after mix for 10 days. FIG. 3A shows that the mixture of the deep-sea water concentrate liquid and the skincare formulas has white lump precipitates after the deep-sea water concentrate liquid and skincare product gel are mixed for 10 days. FIG. 3B shows that the gel is disintegrated after the deep-sea water concentrate liquid and the skincare gel are mixed for 10 days, and viscosity of the gel is reduced significantly. FIG. 3C shows the cream is disintegrated after the deep-sea water concentrate liquid and the skincare cream are mixed for 10 days, and the viscosity of the cream is reduced significantly.

FIG. 5A shows particle sizes of the deep-sea water concentrate liquid measured by a dynamic light scattering analyzer. FIG. 5B shows the mixture of the deep-sea water concentrate and the skincare gel mixed immediately with a weight ratio of 1:1 measured by a dynamic light scattering analyzer.

DESCRIPTION OF THE PREFERRED EMBODIMENTS

Figure 1A:
FIGS. 1A to 1C are pictures showing changes of a wound after the deep-sea water concentrate skin application set is applied to the wound.

The following embodiments of the present invention are herein described in detail with reference to the accompanying drawings. These drawings show specific examples of the embodiments of the present invention. It is to be understood that these embodiments are exemplary implementations and are not to be construed as limiting the scope of the present invention in any way. Further modifications to the disclosed embodiments, as well as other embodiments, are also included within the scope of the appended claims. These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts.

It is to be understood that, although the terms 'first', 'second', 'third', and so on, may be used herein to describe various elements, these elements should not be limited by these terms. These terms are used only for the purpose of distinguishing one component from another component. Thus, a first element discussed herein could be termed a second element without altering the description of the present disclosure. As used herein, the term "or" includes any and all combinations of one or more of the associated listed items.

It will be understood that when an element or layer is referred to as being "on," "connected to" or "coupled to" another element or layer, it can be directly on, connected or coupled to the other element or layer, or intervening elements or layers may be present. In contrast, when an element is referred to as being "directly on," "directly connected to" or "directly coupled to" another element or layer, there are no intervening elements or layers present.

In addition, unless explicitly described to the contrary, the word "comprise" and variations such as "comprises" or "comprising" will be understood to imply the inclusion of stated elements but not the exclusion of any other elements.

The present invention provides a deep-sea water concentrate skin application set.

In the present invention, the deep-sea water (DSW) means the seawater obtained from 200 m to 1500 m under the surface of the sea. Preferably, the deep-sea water is the seawater obtained from 500 m to 700 m under the surface of the sea. Each 100 g of deep-sea water contains calcium in a range from 1000 mg to 1500 mg, magnesium in a range from 1,400 mg to 2,100 mg, sodium in a range from 2,000 mg to 4,000 mg, potassium of range of 1,400 mg to 2,100 mg, sulfate lower than 6.5 wt %, and solution of sea minerals with density in a range from 1.17 $g/cm^3$ to 1.32 $g/cm^3$.

In the present invention, the "deep-sea water concentrate" means the liquid or powder generated from the deep-sea water after a concentration process. The process of concentrating the deep-sea water concentrate liquid or powder can be performed by a fiber filtration system, an ultrafiltration system, a seawater reverse osmosis system, a low-temperature vacuum evaporation concentrating system, and/or a centrifugal manner.

The concentration of the deep-sea water concentrate is in a range from 80,000 mg/l to 420,000 mg/l, the salinity of the deep-sea water concentrate is in a range from 380‰ to 430‰, the concentration of magnesium is in a range from 6,500 mg/l to 110,000 mg/l, and the concentration of sodium is in a range from 3,800 mg/l to 30,000 mg/l. The deep-sea water concentrate is rich in various minerals including, but not limited thereto, trace elements such as calcium (Ca), potassium (K), potassium (K), iron (Fe), zinc (Zn), molybdenum (Mo), manganese (Mn), lithium (Li), strontium (Sr), copper (Cu), silicon (Si). In an embodiment, Table 1 shows components of deep-sea water concentrate; however, the testing agency does not test all of the elements, so the deep-sea water concentrate of the present invention is not limited to the components shown in Table 1.

TABLE 1

| Components of the deep-sea water concentrate | | | | | |
|---|---|---|---|---|---|
| | Formula 1 | Formula 3 | | Formula 1 | Formula 3 |
| potassium | 0.53% | 1.4% | $HCO_3$ | N/A | N/A |
| calcium | 13.9 ppm | 8.92 ppm | carbonate | N/A | N/A |
| titanium | 0.03 ppm | N.D. | aluminum | N.D. | N.D. |
| vanadium | 2.21 ppm | 0.54 ppm | antimony | N.D. | N.D. |
| manganese | N.D. | N.D. | arsenic | 1.52 ppm | 0.13 ppm |
| iron | 0.09 ppm | 0.04 ppm | beryllium | N.D. | N.D. |
| copper | 0.03 ppm | 0.02 ppm | boron | 235.1 ppm | 0.31 ppm |
| zinc | 0.53 ppm | N.D. | chromium | 0.30 ppm | 0.14 ppm |
| bromine | N.D. | N.D. | cobalt | 0.22 ppm | 0.03 ppm |
| strontium | N.D. | N.D. | molybdenum | 0.59 ppm | 0.29 ppm |
| lead | N.D. | N.D. | nickel | 0.26 ppm | 0.07 ppm |
| cadmium | N.D. | N.D. | mercury | N.D. | N.D. |
| magnesium | 9.1% | 4.6% | barium | N.D. | N.D. |
| selenium | N.D. | N.D. | fluorine | N.D. | N.D. |
| lithium | 29.74 ppm | 9.3 ppm | iodine | 3.8 ppm | 1.0 ppm |
| sodium | 0.53% | 10% | $SO_4$ | N.D. | N.D. |

The skincare formula of the present invention means the formula used in general commercial skincare product and the formulas used in treatment of beauty salon, and the formula of the present invention is not limited. For example, the formula can be cream or gel product, such as whiting product, moisturizer product, anti-wrinkle product, wound healing product, product used in fast healing treatment to improve skin appearance.

In the present invention, the mixture of the deep-sea water concentrate and the skincare formulas, or the deep-sea water concentrate mixture means the mixture body of the deep-sea water concentrate and the skincare formulas. After the sea-water concentrate is added into the gelatinous or creamy skincare product, phase transfer possibly occurs immediately and the molecule become smaller, so the skincare product can reach deep layer of skin to be absorbed by skin easily for making effective.

However, after the deep-sea water concentrate is added into the skincare formulas for a period of time, the deep-sea water concentrate can cause metamorphism, instability, and disintegration of the skincare formulas. For this reason, preferably, the mixture of the deep-sea water concentrate of the present invention and mixture is freshly manufactured. Preferably, the mixture is used within 9 days, 8 days, 7 days, 6 days, 5 days, 4 days, 3 days, 2 days, or 1 day. Most preferably, the mixture is used within 12 hours, 6 hours, 3 hours, 2 hours or 1 hour.

After the deep-sea water concentrate is mixed with the skincare formulas, the surface tension of the mixture of the deep-sea water concentrate and skincare formulas can be improved, so as to increase adsorption of the skin (dermis) on skincare application kit. As a result, the mixture can be adsorbed by skin easily and reach dermis to be effective.

The present invention also provides a method of improving permeability of a skincare formula, and the method comprises providing the skincare formula, and mixing the skincare formula and a deep-sea water concentrate before use.

The mixing manner applied in the present invention is not limited, and can be general manner, for example, stirring manner, shaking manner, test tube oscillation, or ultrasonic oscillation; any manner capable of uniformly mixing the skincare formula and the deep-sea water concentrate can be applied in the present invention. The mixing period is not limited in the present invention. Since the mixture must be used to prevent deterioration of skincare formula quality, the mixing period shall not be too long. Generally, the mixing period is shorter than 15 minutes, and preferably, the mixing period can be 14 minutes, 13 minutes, 12 minutes, 11 minutes, 10 minutes, 9 minutes, 8 minutes, 7 minutes, 6 minutes, 5 minutes, 4 minutes, or 3 minutes. The mixing period can be adjusted upon the skincare formula and the mixing manner.

According to above-mentioned content, after the deep-sea water concentrate is mixed with the skincare formula, the mixture must be applied to the skin as soon as possible, so as to avoid the change in skincare formula quality.

After the deep-sea water concentrate is added into skincare formula, the gel and cream skincare product can be deteriorated obviously after 10 days merely. Furthermore, the deep-sea water concentrate causes the gel skincare product to produce unknown precipitate and float, which indicates that when the deep-sea water concentrate is directly added into the skincare formula for a period of time, the ionic minerals of the deep-sea water concentrate may have chemical reaction with component of the skincare formula. This reduces the effect of the original skincare formula on the skin, and even produce harmful derivative for the skin. For this reason, the deep-sea water concentrate and skincare product must be packaged independently, and just mixed before use, so as to obtain a multiplicative effect.

After the deep-sea water concentrate is added into skincare formula, phase transfer possibly occurs immediately to make the molecules of the skincare product become smaller, so that the skincare formula can reach dermis to be absorbed by skin easily. As a result, the deep-sea water concentrate can improve permeability of the skincare formula on the skin, thereby making the skincare formula effective more quickly.

The present invention further provides a method of caring skin, and the method comprises applying the manufactured deep-sea water concentrate mixture to the skin immediately after the deep-sea water concentrate mixture of the present invention is manufactured. After the deep-sea water concentrate mixture of the present invention is applied to the skin or treated into the skin by instrument, the deep-sea water concentrate mixture can quickly reach the inside of skin to be adsorbed by body and to be effective.

Embodiments

Embodiment of the method of manufacturing the deep-sea water concentrate:

The method of manufacturing the deep-sea water concentrate includes the following steps. First, deep-sea water obtained from a predetermined depth under the surface of the sea is provided, and a fiber filtration system, the ultrafiltration system, and the seawater reverse osmosis system are used in a sequential order to filter the deep-sea water, thereby obtaining first concentrate and pure water. Next, first concentrate can be further concentrated by low-temperature vacuum evaporation concentrating system so as to obtain second concentrate and calcium sulfate (plaster). The low-temperature vacuum evaporation concentrating system is a circulation system, so the second concentrate can be concentrated continuously by this system. During the concentration process, the second concentrate produces crystalline salt group, so solid particle salts (such as deep-sea salt) and third concentrate can be obtained in a centrifugation manner. The third concentrate can be heated at a predetermined temperature in a range from 90° C. to 120° C. During the heating process, crystalline salt is continuously extracted from the third concentrate. After the heated third concentrate is placed, the crystalline salt can settle at the bottom, and so the supernatant can be drawn so as to obtain the fourth concentrate. Finally, a membrane filter having predetermined hole diameter in a range from 0.5 μm to 1.5 μm can be used to filter the cooled fourth concentrate so as to obtain the deep-sea water concentrate.

The deep-sea water concentrate with different property can be mixed with different skincare formula to manufacture deep-sea water concentrate mixture with different effect so as to optimizing the whiting, moisturizing, anti-wrinkle, wound healing effect, and so on.

The deep-sea water concentrate liquid or powder of various formulas can be manufactured according to the aforementioned process. Table 2 shows a reasonable interval selected from the formulas.

TABLE 2

The contents of components of the deep-sea water concentrate liquid/powder of different formulas

|  | Formula 1 | Formula 2 | Formula 3 |
|---|---|---|---|
| Deep-sea water concentrate (liquid/powder) | 170,000 PPM | 200,000 PPM | 400,000 PPM |
| magnesium | 40K-50K mg/L | >49,000 PPM | 90K-110K mg/L |
| sodium | 20,000~30,000 mg/L | <16K PPM | 6,000~9,000 mg/L |
| potassium | 7,000~10,000 mg/L | <18,000 PPM | 7,000~10,000 mg/L |
| calcium | <500 mg/L | <200 PPM | <200 mg/L |

|  | Formula 4 (powder) | Formula 5 (powder) |
|---|---|---|
| Deep-sea water concentrate (liquid/powder) | 80,000 PPM | 150,000 PPM |
| magnesium | 6.5K-12K ppm | 15K-20K ppm |
| sodium | 3.8K-6K ppm | 7K-11K ppm |
| potassium | >400 ppm | 4K-6K ppm |
| calcium | >200 ppm | >100 ppm |

Embodiment One: Wound Experiment

In this experiment, the mixture of the deep-sea water concentrate and skincare gel mixed immediately is applied to an injured leg, and a change in the wound is observed.

Figure 1B:
Figure 1C:

Please refer to FIGS. 1A to 1C. The leg is injured at 10:16 am, on Sep. 23, 2017, as shown in FIG. 1A, and the skin application set of the deep-sea water concentrate liquid/powder mixing with the skincare gel immediately is applied to the wound after wound disinfection at 3:56 pm, as shown in FIG. 1B. At 10:45 pm, the red and swollen wound is detumescent, and the wound does not scab, as shown in FIG. 1C.

As a result, the mixture of the skincare gel and the deep-sea water concentrate can be adsorbed by the skin easily, so as to improve wound healing.

Embodiment Two: The Effect of the Deep-Sea Water Concentrate on the Permeability of Skincare Cream and Gel A quantitative dropper is used to draw mixture of the deep-sea water concentrate and cream or gel with equal amounts. The control groups include (a) water, (b) deep-sea water concentrate liquid, (c) gel, and (D) cream. The experimental groups are 1 mL deep-sea water concentrates, which are 1× concentrated, 5× concentrated, 10× concentrated, 20× concentrated, and 40× concentrated, respectively, mixed with 1 mL cream or gel. The effective concentrations of the deep-sea water concentrate mixtures are 50 (v/v) %, 10 (v/v) %, 5 (v/v) %, 2.5 (v/v) % and 1.25 (v/v) %.

In the permeability test on a regular cloth AATCC97, the 0.5 mL mixture is dropped on the regular cloth AATCC97 from a height of 1 cm. After the mixture of deep-sea water concentrate and gel is dropped, the time for the mixture to fully permeate the test cloth is counted. On the other hand, after the mixture of the deep-sea water concentrate and cream is dropped, the permeability of the mixture is observed every 2 minutes, and the observation results are shown in Table 2A.

TABLE 2A

Comparison of permeability of mixture of the skincare product and the deep-sea water concentrate before mix and after mix

| Before mix (control groups) | | | | |
|---|---|---|---|---|
| Sample | (a) water | (b) deep-sea water concentrate | (c) skincare gel | (d) skin care cream |
| Result | 1 second | Fully adsorbed after 6 minutes and 49 seconds | Spread to about 3 times of area after 5 minute | Not spread after 5 minutes |

| After mix (experimental groups) | | |
|---|---|---|
| Sample | Deep-sea water concentrates, which are 1X concentrated, 5X concentrated, 10X concentrated, 20X concentrated, and 40X concentrated, mixed with skincare gel | Deep-sea water concentrates, which are 1X concentrated, 5X concentrated, 10X concentrated, 20X concentrated, and 40X concentrated, mixed with skincare cream |
| Result | Fully adsorbed after 5 seconds | Spread to 4 times of area after 5 minutes |

The ionic deep-sea water concentrate liquid has been demonstrated by documents to have whiting and anti-aging effect for skin cell; however, the experiment result of (b) deep-sea water concentrate liquid shows that the deep-sea water concentrate is not easy to permeate skin cell to be adsorbed subject to high surface tension thereof.

However, after the deep-sea water concentrate and the skincare gel or skincare cream are mixed by a volume ratio of 1:1, molecular groups of the deep-sea water concentrate become smaller. Therefore, permeability of adsorption of the skincare product can be improved, and the problem that the deep-sea water concentrate is not easy to be adsorbed by skin because of high surface tension thereof can be solved. As a result, the permeability and adsorption of skin can be improved to provide better skincare effect.

Figure 2A:
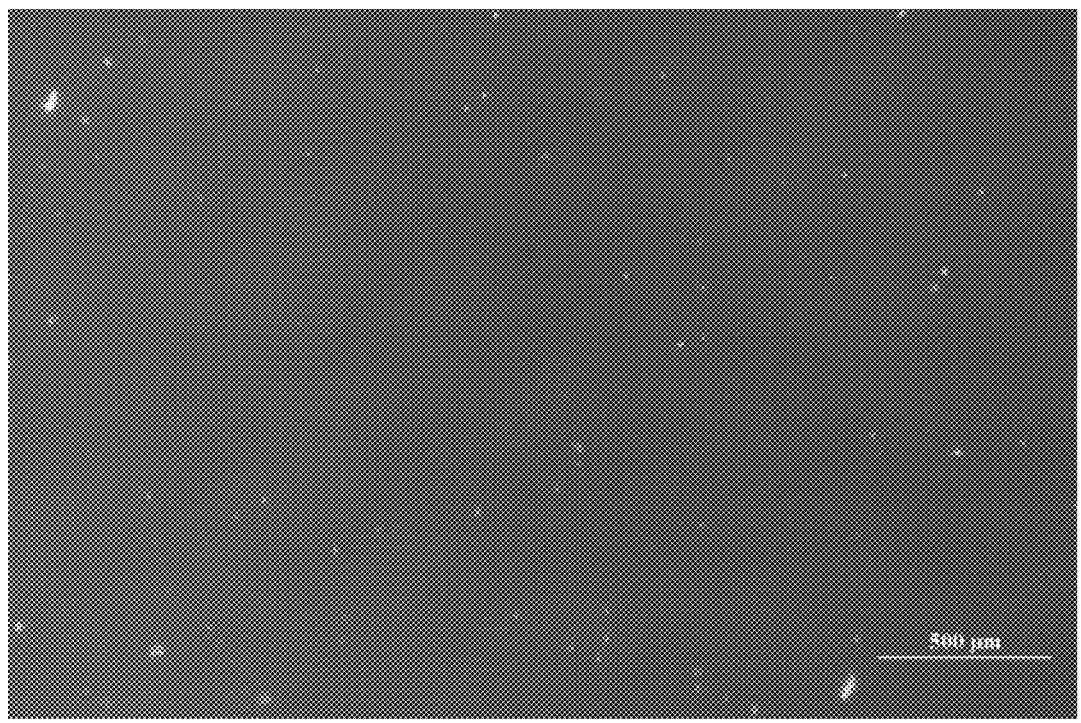
FIGS. 2A to 2G show pictures shot by 40× and 200× optical microscope, for observing deep-sea water concentrate liquid (FIG. 2A), skincare gel, (FIG. 2B), skincare cream, (FIGS. 2C and 2D), mixture of the deep-sea water concentrate liquid and the skincare gel mixed immediately with a volume ratio of 1:1 (FIGS. 2E and 2F), mixture of the deep-sea water concentrate liquid and the skincare cream mixed immediately with a volume ratio of 1:1 (FIGS. 2G and 2H), mixture of the deep-sea water concentrate liquid and skincare gel mixed and placed for 3 hours with a volume ratio of 1:1 (FIGS. 2I and 2J), mixture of the deep-sea water concentrate liquid and skincare cream mixed and placed for 3 hours with a volume ratio of 1:1 (FIGS. 2K and 2L), respectively.

Embodiment Three: The Effect of the Deep-Sea Water Concentrate on the Skincare Formulas The ITRI material and chemical research laboratories are commissioned to perform this experiment. In this experiment, an optical microscope is used to capture picture of deep-sea water concentrate (as shown in FIG. 2A), skincare gel (as shown in FIG. 2B), skincare cream (as shown in FIG. 2C), mixture of the deep-sea water concentrate and the skincare gel mixed immediately with a volume ratio of 1:1 (as shown in FIG. 2D), mixture of the deep-sea water concentrate liquid and the skincare cream mixed immediately with a volume ratio of 1:1 (as shown in FIG. 2E), the mixture of deep-sea water concentrate liquid and skincare gel with a volume ratio of 1:1 and placed for 3 hours (as shown in FIG. 2F), the mixture of deep-sea water concentrate liquid and skincare cream with a volume ratio of 1:1 and placed for 3 hours (as shown in FIG. 2G).

Figure 2B:
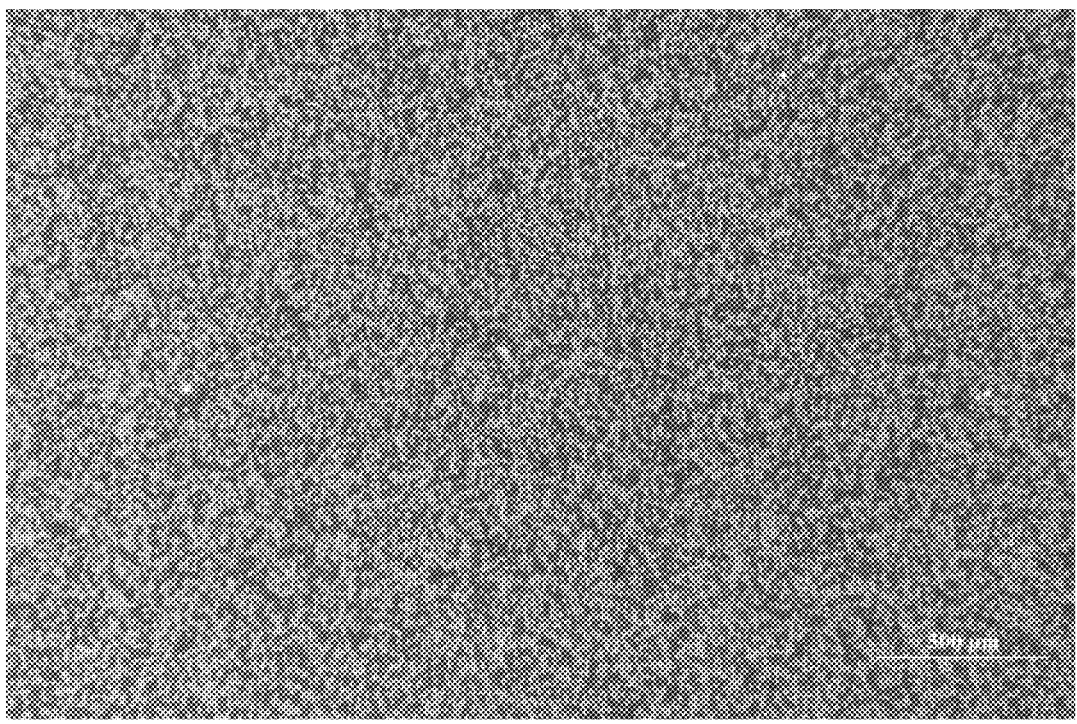
Figure 2C:
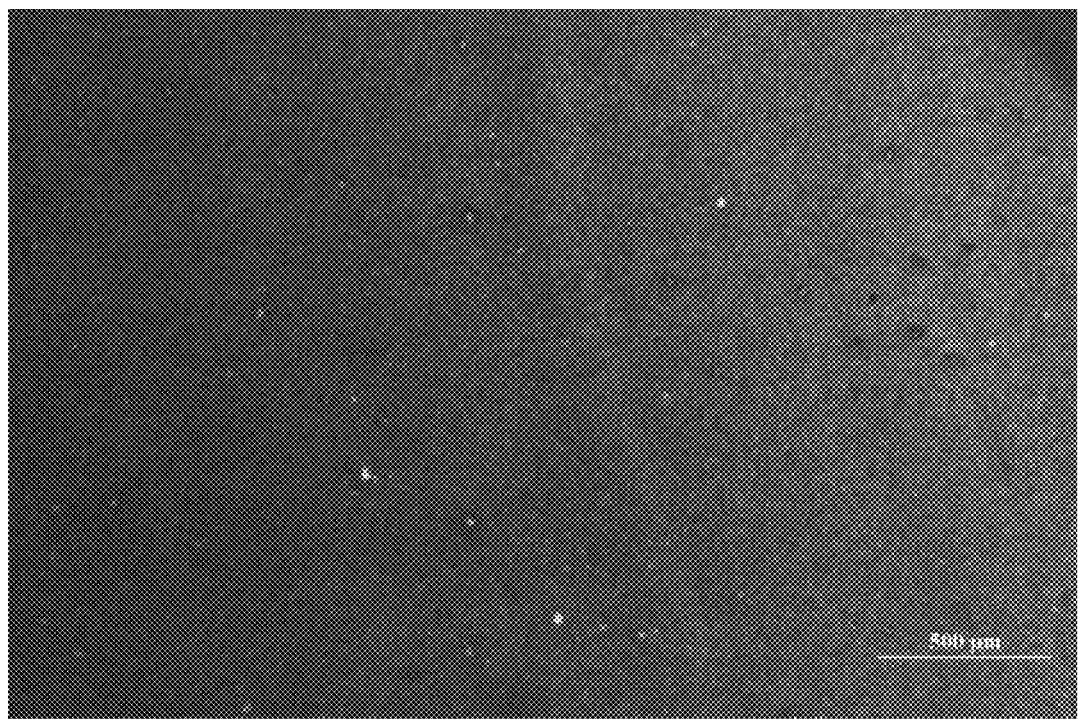
Figure 2D:
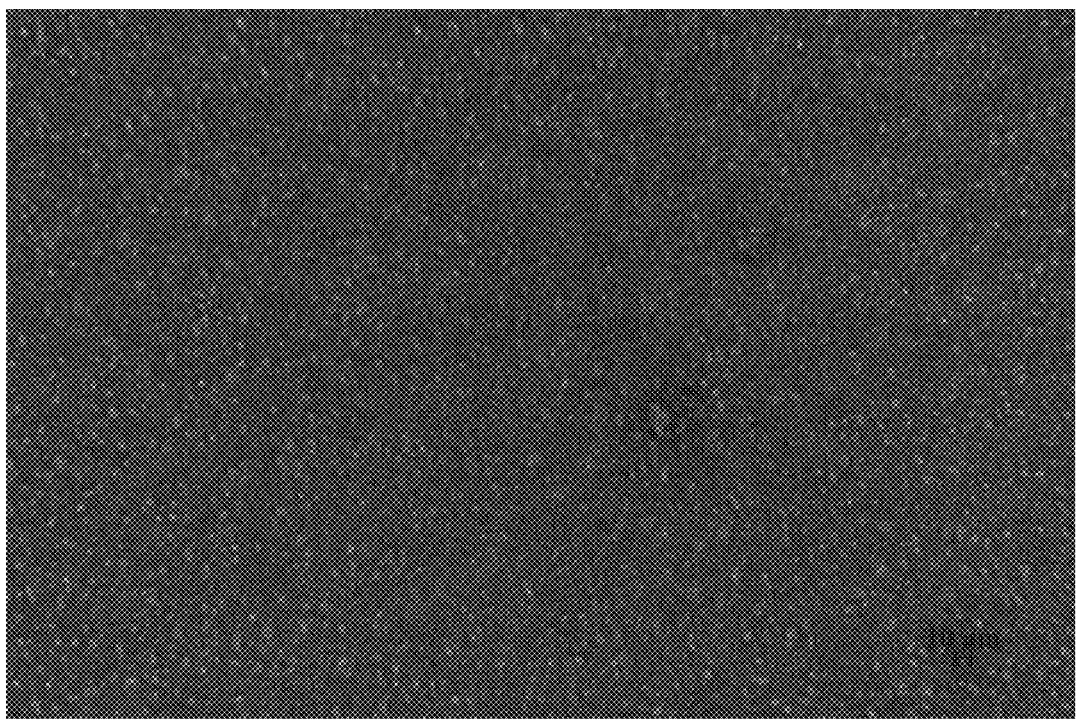

In observation of using 40× microscope, the skincare gel (as shown in FIG. 2B) and skincare cream (as shown in FIG. 2C) have molecular groups formed tightly and no granular particle. In observation of skincare cream by 200× microscope, as shown in FIG. 2D, there is not obvious granular particle.

Figure 2E:
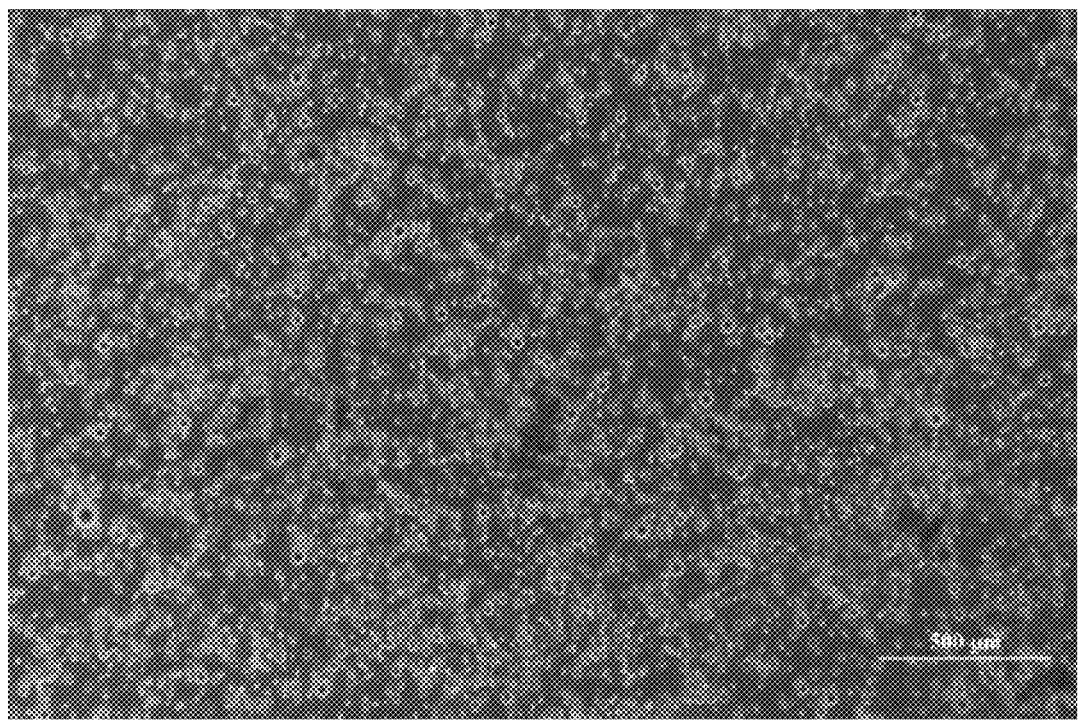
Figure 2F:
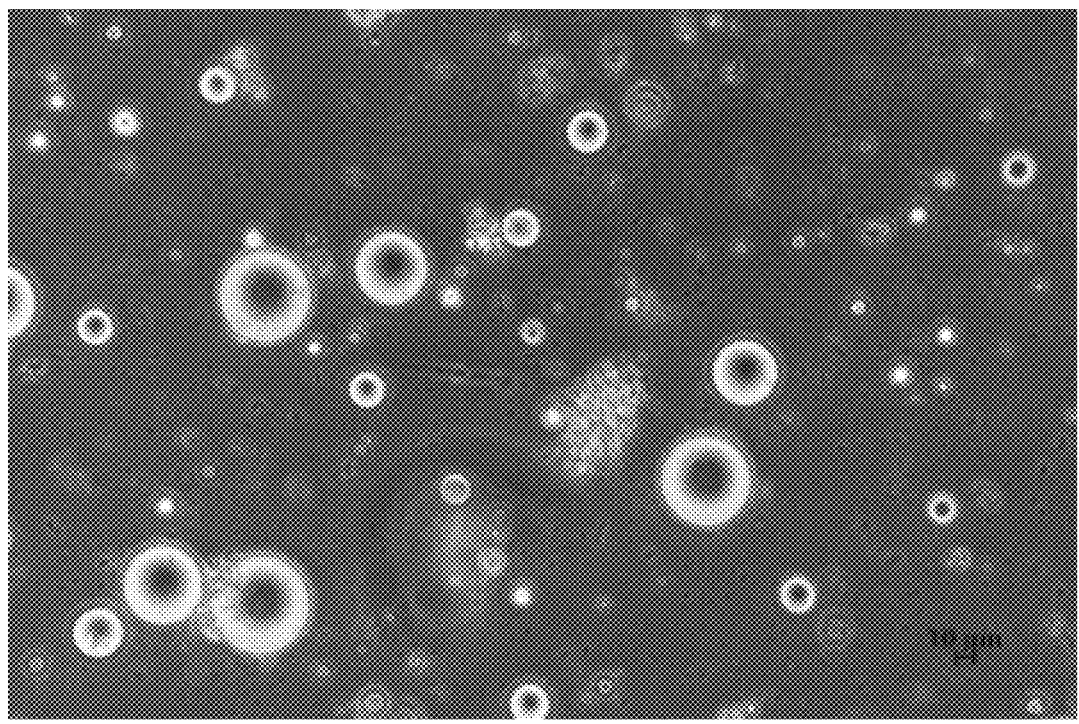
Figure 2G:
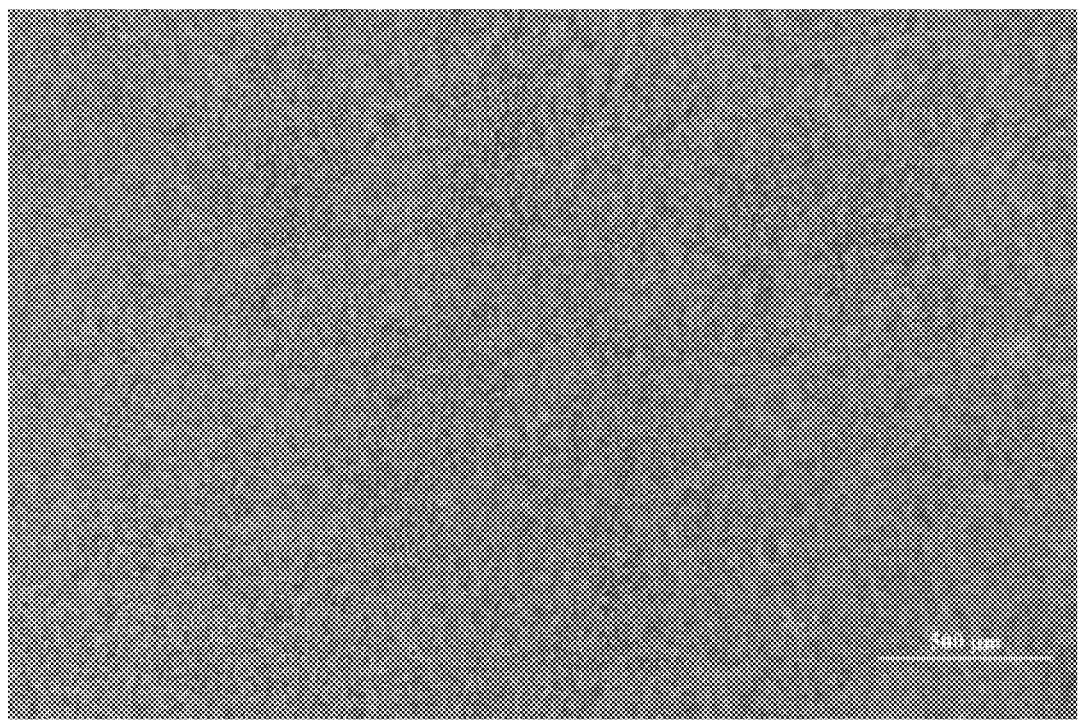
Figure 2H:
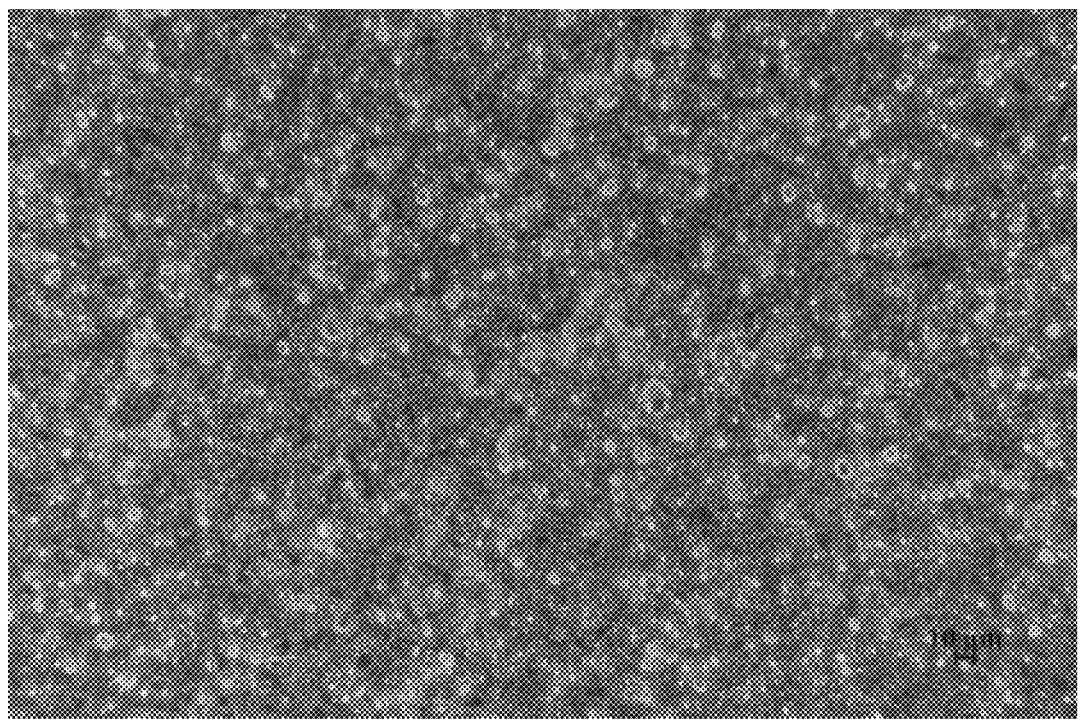

In observation of, by using 40× and 200× microscopes, the mixture of deep-sea water concentrate and the skincare gel mixed immediately (as shown in FIGS. 2E and 2F), and the mixture of deep-sea water concentrate and the skincare cream mixed immediately (as shown in FIGS. 2G and 2H), the skincare gel and skincare cream having molecular groups formed tightly are micronized by ionic minerals, to have only a third of original sizes or lesser, and distribute uniformly. In conclusion, when the deep-sea water concentrate is immediately mixed with the skincare gel or skincare cream, the mixture has clear particles, and oil and water are mixed uniformly, so that the mixture can be adsorbed by skin more easily.

Figure 2I:
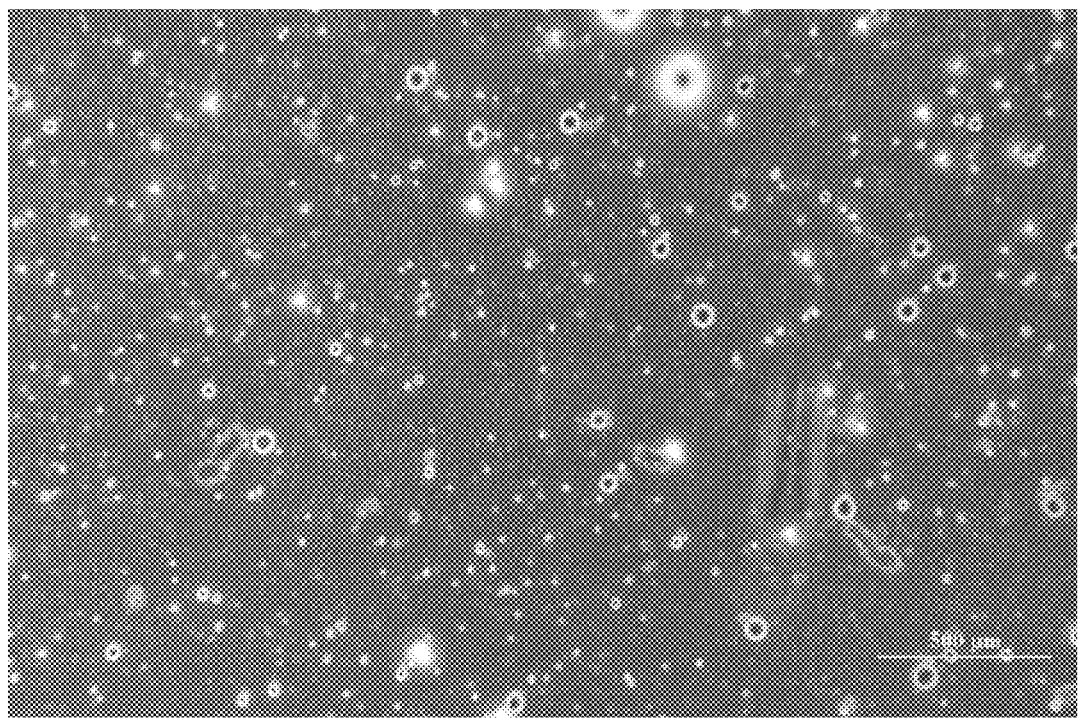
Figure 2J:
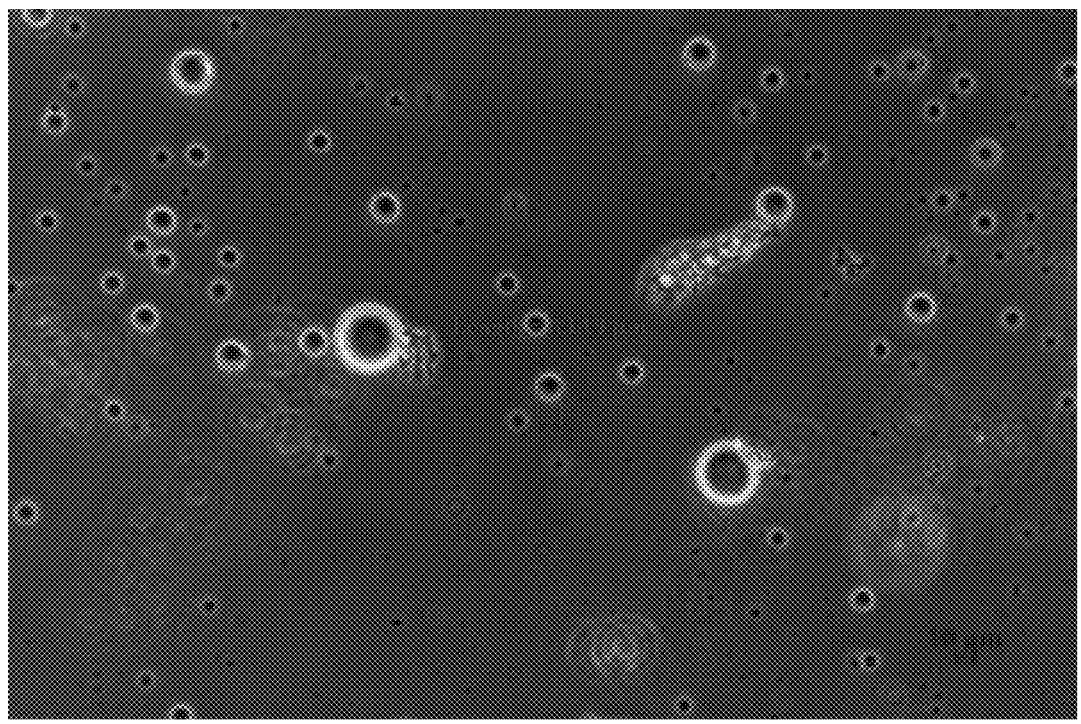
Figure 2K:
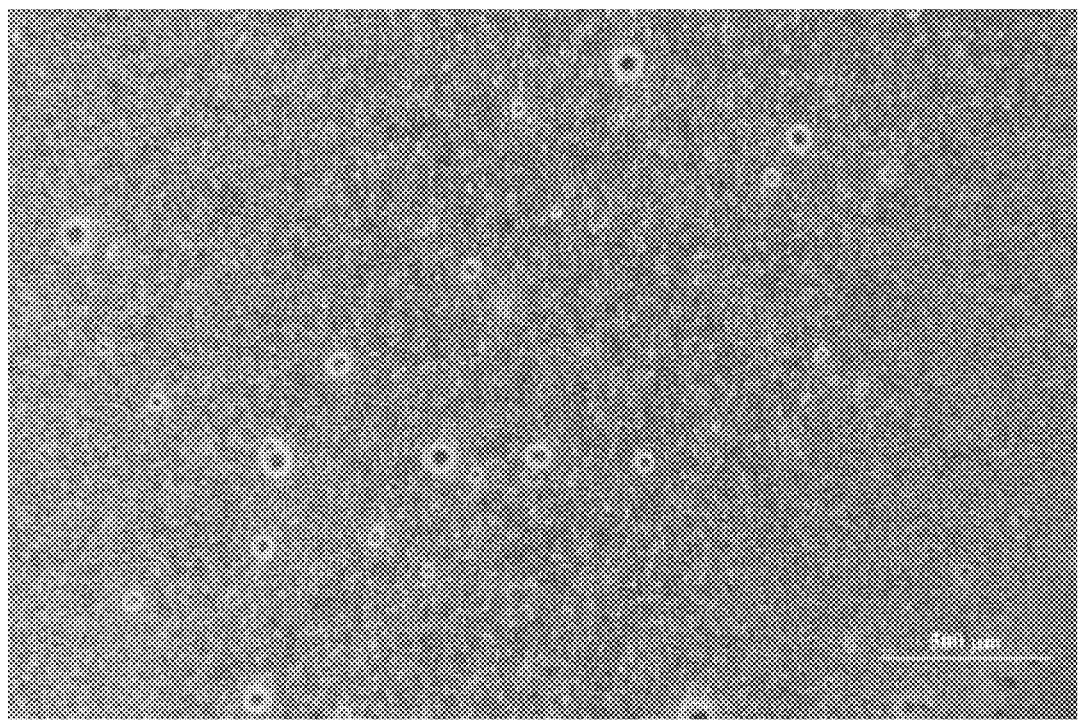
Figure 2L:
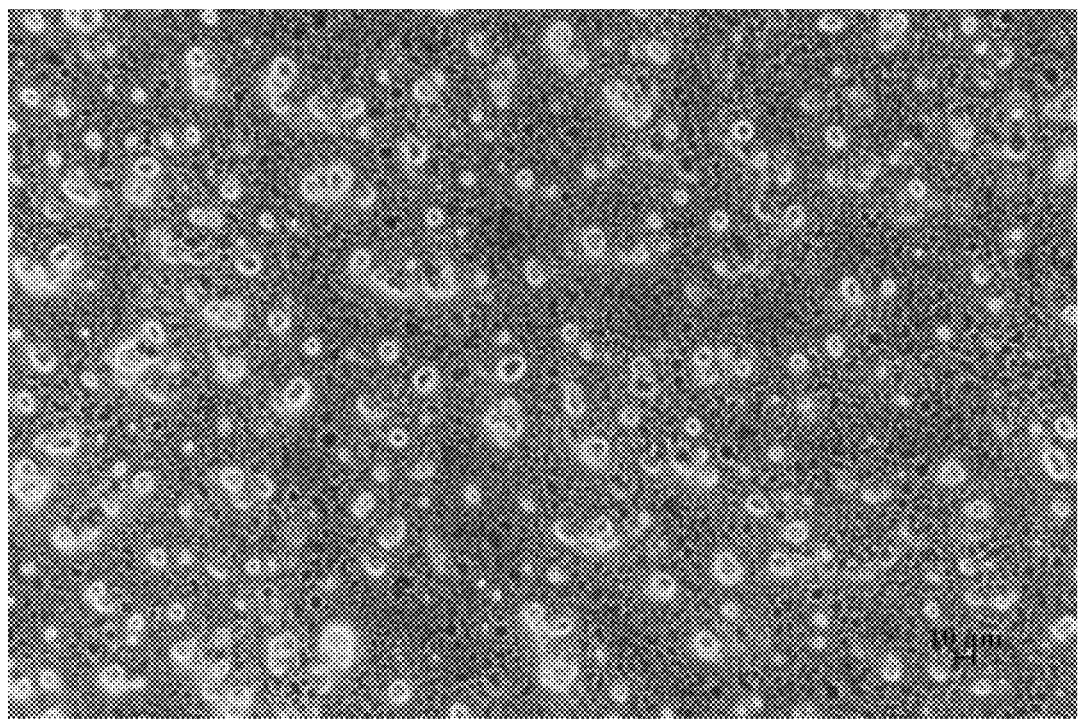

However, in observation of, using 40× and 200× microscopes, the mixture of deep-sea water concentrate and skincare gel mixed for 3 hours (as shown in FIGS. 2I and 2J), and the mixture of deep-sea water concentrate liquid and skincare cream mixed for 3 hours (as shown in FIGS. 2K and 2L), molecular groups are clustered to become larger. Furthermore, in observation of, using 200× microscopes, the mixtures of deep-sea water concentrate liquid and skincare gel and skincare cream mixed for 3 hours (as shown in FIGS. 2I and 2J), the clustering of molecular groups is more significant, so such mixtures are more difficult to be adsorbed by skin.

According to above-mentioned experiment results, the deep-sea water concentrate of the present disclosure can provide effect of immediately micronizing the skincare formula. Each of the skincare gel and skincare cream is heavy molecule and have molecular groups formed tightly, so the skincare gel and the skincare cream are not easy to be adsorbed by skin. However, after the mixture of deep-sea water concentrate liquid and skincare gel/cream is placed for a period of time, clustering of molecular groups occurs, so the mixture is more difficult to be absorbed by skin. Only when being mixed immediately, the molecules of the deep-sea water concentrate liquid and skincare gel/skincare cream can be micronized and mixed uniformly, so as to be adsorbed by skin more easily.

Embodiment Four: Effect of Deep-Sea Water Concentrate on Viscosity and Stability of Skincare Cream and Gel In the embodiment four, 1 mL cream and 1 mL gel are filled into microcentrifuge tubes, separately, and are centrifugated by 2000 rpm for 5 minutes, and the deep-sea water concentrate is diluted 1 times, 5 times, 10 times, 20 times and 40 times, respectively, by using sterilized ultrapure water. 1 mL deep-sea water concentrates diluted different times are added into microcentrifuge tubes where 1 mL cream or 1 mL gel are filled, for further mixing. The control groups include (a) 1 mL ultrapure water mixed with 1 mL gel, and (b) 0.5 mL ultrapure water mixed with 0.5 mL cream. The experimental groups include 1 mL cream or 1 mL gel mixed with 1 mL deep-sea water concentrates, which are 1×, 5×, 10×, 20× and 40× concentrated, respectively. The effective concentrations of the deep-sea water concentrate mixtures are 50 (v/v) %, 10 (v/v) %, 5 (v/v) %, 2.5 (v/v) % and 1.25 (v/v) %, respectively. The mixture is mixed uniformly by using a test tube oscillator, and the microcentrifuge tubes filled with the mixture are then placed on a test tube frame at room temperature for 10 days. The viscosity of mixture is measured by using a glass capillary tube. The microcentrifuge tube filled with mixture is fastened on a desktop, and a glass capillary tube is inserted into the microcentrifuge for 1 minute, and the capillary tube is then taken out from the microcentrifuge tube to measure a height of fluid in the capillary tube.

Figure 3A:
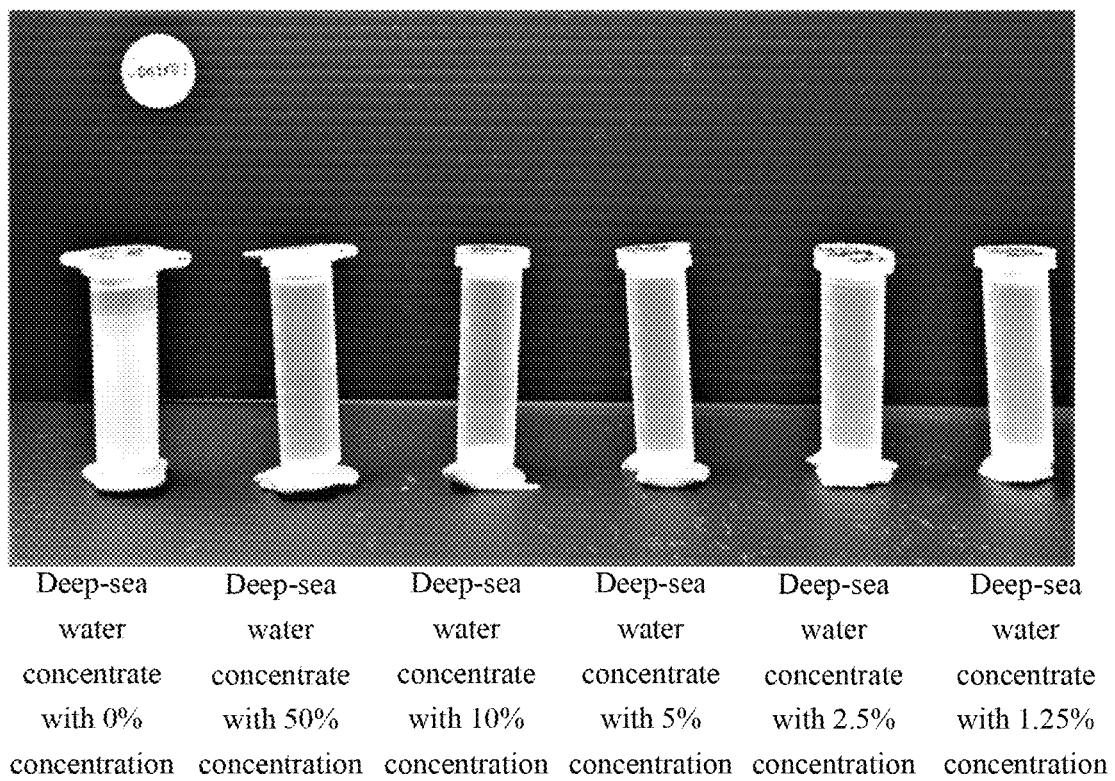

Please refer to FIG. 3A. The viscosity of skincare gel in the mixture of deep-sea water concentrate and skincare gel is obviously changed after 10 days, which indicates that the physical property of the skincare gel is denaturalized. In addition, white lump deposition can be observed by naked eye, which indicates that chemical reaction occurs in the mixture during 10-day still placement.

Please refer to FIG. 3B. The viscosity of skincare cream in the mixture of the deep-sea water concentrate and the skincare cream is reduced significantly in observation of naked eye and experimental test, which indicates that the stability of the skincare cream is changed.

Please refer FIG. 3C. After the deep-sea water concentrate liquid and the skincare gel are mixed for 10 days, the skincare gel is disintegrated, and the viscosity reduces by 100%. As shown in FIG. 3C, when the skincare gel is not mixed with deep-sea water concentrate liquid, the height of fluid in the capillary tube is 1.5 cm, which indicates the fluid is glue phase. When the skincare gel is mixed with the deep-sea water concentrate having a high or low concentration and even the skincare gel is mixed with the deep-sea water concentrate diluted 40 times (The concentration of the deep-sea water concentrate liquid is 1.25%), the heights of the fluids in the capillary tube are 3 cm. This indicates that the skincare gel is changed to aqueous phase.

According to above-mentioned content, the deep-sea water concentrate liquid/powder can cause skincare formulas to have oil and water separation and be in instable state. The mixture possibly produces chemical crystalline to have qualitative change during long-term preservation, and it is hard to confirm that such mixture is still helpful for skin healthy. For this reason, the mixture of the deep-sea water concentrate and the skincare cream cannot be preserved for long term. The most preferable usage manner is to mix the deep-sea water concentrate and the skincare cream/gel with equal amounts and immediately apply the mixture to skin.

Figure 4A:
FIGS. 4A to 4B show that the electron iontophoresis instrument applies the deep-sea water concentrate skin application set to a patient's face, for reducing freckles and lines on the face.
Figure 4B:
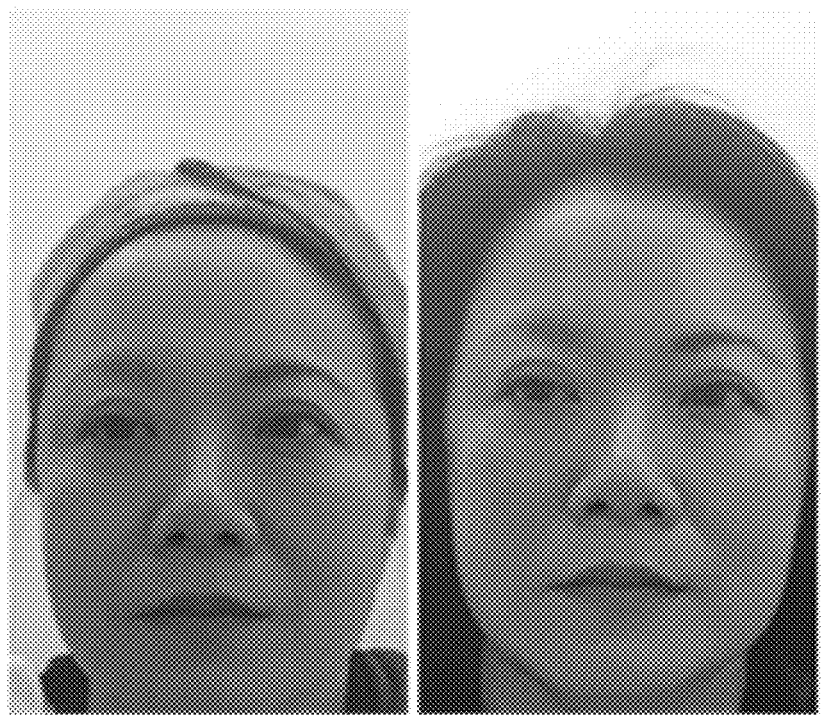

Embodiment Five: The Non-Invasive Water Light Needle Treatment Test Using the Mixture of the Sea-Water Concentrate and the Skincare Gel Mixed Immediately On Oct. 15, 2017, a medical-grade electron iontophoresis instrument is used to treat a user's right face with the mixture of the sea water concentrate and skincare gel mixed immediately. On October 26, the treatment is performed on the right face again. On October 15, after the treatment is performed, the right face become reddish. This indicates that the more-concentrated ions of deep-sea water concentrate permeate into dermis even basal layer after treatment, and introduce increasing of blood circulation in local microvasculature in deep layer of skin and the skin temperature increases slightly, and it can effectively promote metabolic rate of skin. The red skin will disappear after several hours, and the right face can have firm and smooth skin texture, as shown in FIG. 4A. On October 26, the treatment is performed on the right face again. The right face is lifted obviously and a height of eyebrow is changed after treatment, as shown in FIG. 4B. Table 3 lists the comparison results of ratios of face texture, surface speckle, porphyrin and brown speckle before and after treatment.

TABLE 3

Comparison of the face skin before and after treatment

|  | Oct. 15 | Oct. 26 | Change |
|---|---|---|---|
| Texture | 51% | 61% | 10% |
| Surface speckle | 88% | 91% | 3% |
| Porphyrin (deep speckle) | 89% | 92% | 3% |
| Brown speckle (basal layer) | 47% | 67% | 20% |

According to the experiment results shown in Table 3, the iontophoresis instrument can be used to treat cells in deep layer. After 24 hours, the effect of improving skin firming and skin gloss and decreasing thin lines can appear. The property of the deep-sea water concentrate can become a driving force for permeability of the micronized skincare formula, so that the skincare formula can be absorbed by skin (dermis) more easily, thereby indeed achieving the effect of quickly caring basal layer, immediately improving water retention capacity of cuticle, and obviously improving skin texture.

Compared with skincare gel only, the skincare gel mixed with sea water concentrate can accelerate skin absorption and quickly reach dermis even basal layer for better treatment effect.

Embodiment Six: Effect of Deep-Sea Water Concentrate on Particle Size of Skincare Gel The ITRI material and chemical research laboratory are commissioned to perform experiment. In this experiment, a dynamic light scattering analyzer is used to measure particle sizes of the deep-sea water concentrate liquid (as shown in FIG. 5A) and the mixture of the deep-sea water concentrate and the skincare gel mixed immediately with a weight ratio of 1:1 (as shown in FIG. 5B).

The dynamic light scattering analyzer can emit laser beam into the solution containing particles, and the laser beam produces scattered light after impacting particle. The change of the scattered light over time can be measured to calculate a particle size distribution of the particles.

Figure 5A:
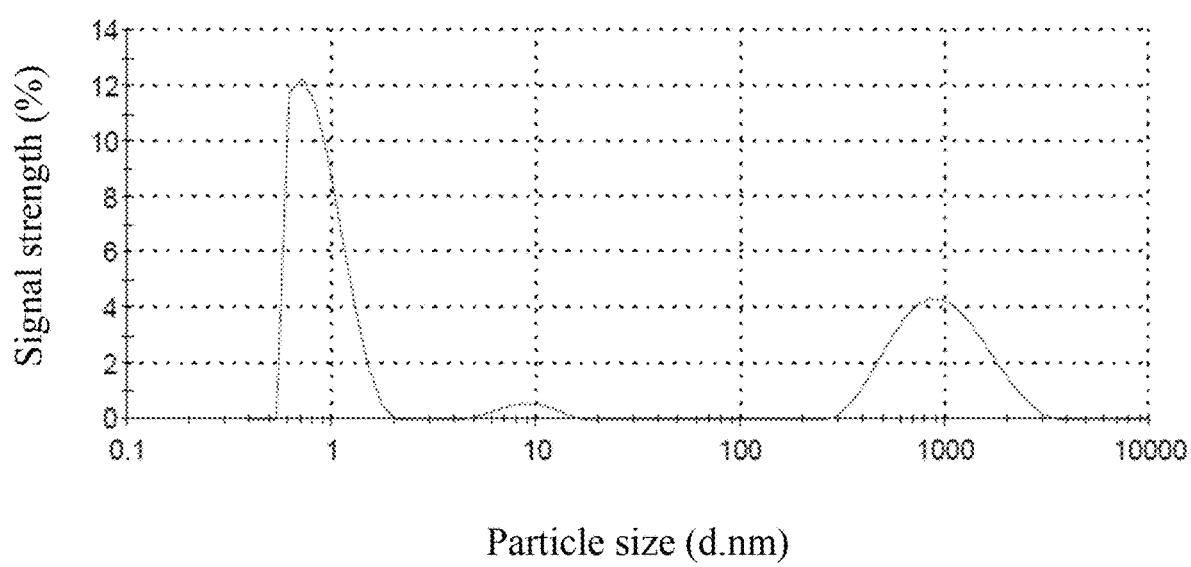
FIGS. 5A to 5B show the laser particle size analysis diagrams.

According to the laser particle size analysis diagram, the 0.89 nm particle of the deep-sea water concentrate has the highest signal in the particle size distribution, as shown in FIG. 5A. An average particle size of the deep-sea water concentrate is 19.2 nm (Z average=19.2 nm), which indicates that the measured sample is a liquid without obvious particle.

Figure 5B:
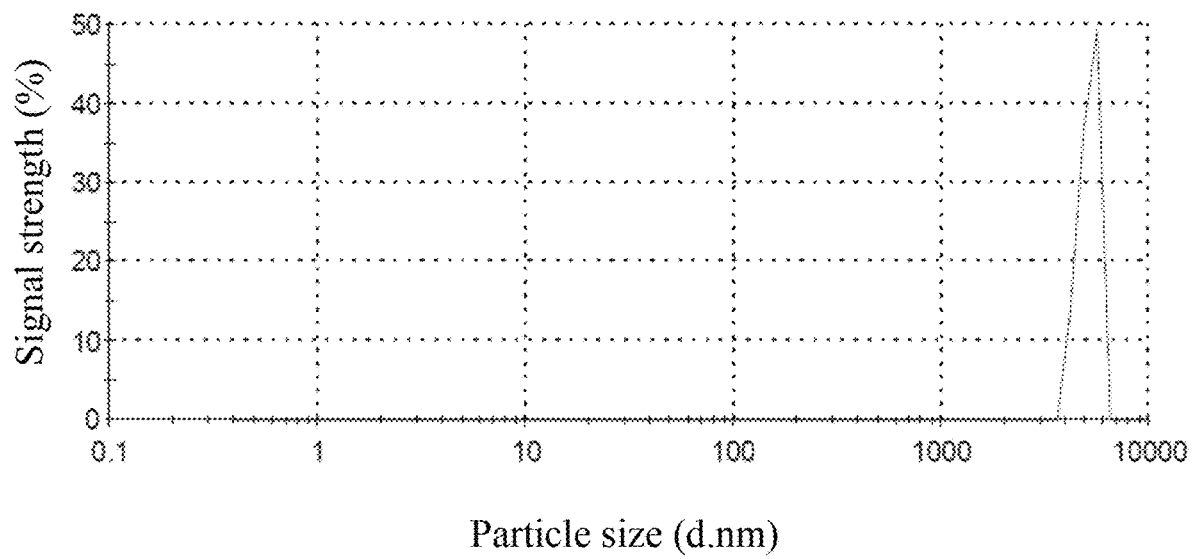

According to the laser particle size analysis diagram, after the deep-sea water concentrate is mixed with skincare gel immediately with a weight ratio of 1:1 (as shown in FIG. 5B), microparticles start to form. 5082 nm of particle has the highest signal value in the particle size distribution, and an average particle diameter is 5.2 μm (Z average=5.2 μm).

As shown in FIG. 5B, the signals of the sample are distributed and centralized, which indicates that microparticles with uniform sizes can be formed immediately after the deep-sea water concentrate liquid and the skincare gel are mixed immediately with the weight ratio of 1:1.

TABLE 4

Laser particle size analysis distribution of mixture of deep-sea water concentrate and skincare gel mixed immediately

| | Particle size (nm) | |
|---|---|---|
| Sample name | Average | Size distribution |
| Deep-sea water concentrate | 19.2 | Peak1: 0.89 (58.1%) |
| | | Peak2: 9.199 (3.1%) |
| | | Peak3: 1029 (38.9%) |
| Deep-sea water concentrate liquid and skincare gel mixed immediately | 5210 | — |

Figure 6A:
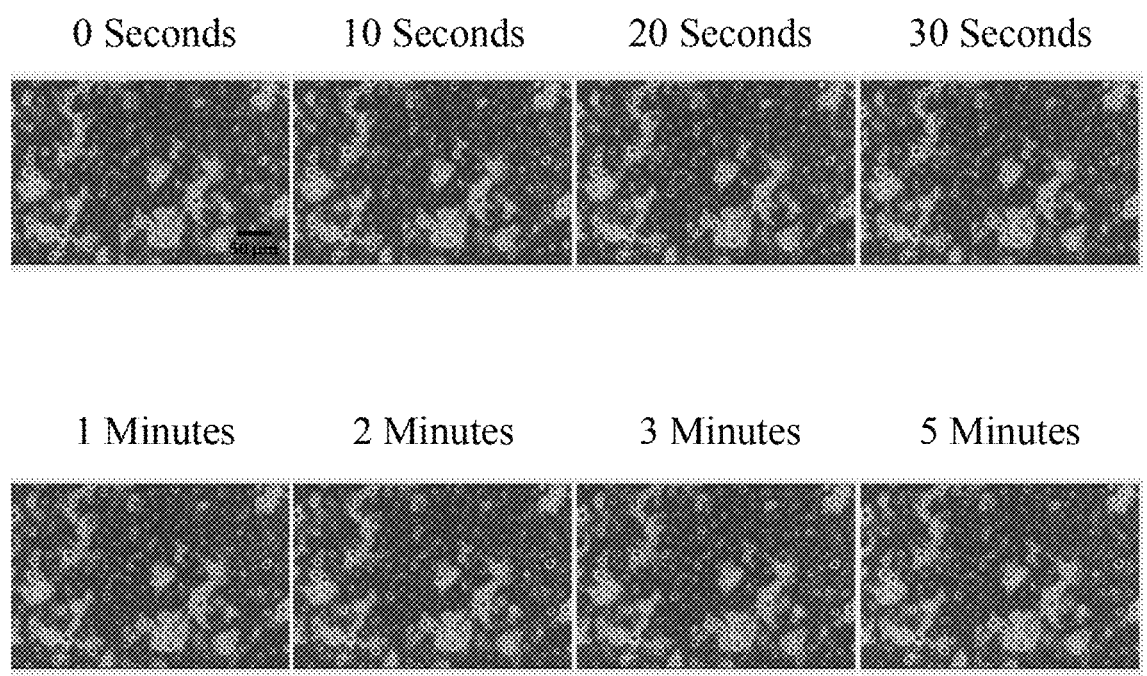
FIGS. 6A to 6D show the change in particle size at different time points after the deep-sea water concentrate liquid and the skincare gel are mixed immediately with a weight ratio of 1:1 (as shown in FIG. 6A) and observations of the difference between microparticles of single dose of skincare gel (as shown in FIG. 6B), a mixture of pure water and skincare gel mixed immediately with a weight ratio of 1:1 (as shown in FIG. 6C), and a mixture of deep-sea water concentrate and skincare gel mixed immediately with a weight ratio of 1:1 (as shown in FIG. 6D) by a 200X optical microscope.

Embodiment Seven: The Effect of Immediately Mixing Deep-Sea Water Concentrate and Skincare Gel on Particle Size in a Short Time Interval The ITRI material and chemical research laboratories are commissioned to perform this experiment. In this experiment, the optical microscope and the dynamic light scattering analyzer are used to observe particle size of the sample, so as to detect the change in particle size at different time points after the deep-sea water concentrate liquid and the skincare gel are mixed immediately with a weight ratio of 1:1, as shown in FIG. 6A.

By using 200× optical microscope to observe, under fixed field of view, the deep-sea water concentrate and the skincare gel mixed immediately with a weight ratio of 1:1, for 0 second, 10 seconds, 20 seconds, 30 seconds, 1 minute, 2 minutes, 3 minutes and 5 minute, it observes that the mixture of the deep-sea water concentrate and skincare gel can maintain sizes of particles within 5 minutes after mixing. The process of forming microparticles of the deep-sea water concentrate liquid and the skincare gel is completed at the 0 second after mixing, and the particle sizes do not change in a short time interval. This indicates that the mixture of the deep-sea water concentrate and the skincare gel mixed immediately can be applied to human skin.

TABLE 5

A laser particle size analysis table for mixture of the deep-sea water concentrate and the skincare gel mixed immediately at different time points.

| Time (minute) after mix | Average particle size (nm) | Coefficient of powder dispersion |
| --- | --- | --- |
| 0 | 5210 | 0.300 |
| 1 | 4566 | 0.453 |
| 3 | 4291 | 0.381 |
| 5 | 5003 | 0.431 |

According to experimental results of optical microscope and laser particle size experiment, the microparticles are formed after the deep-sea water concentrate and the skincare gel are mixed immediately. An average particle size of the microparticles is stable within 5 minutes after mix, which indicates that the sizes of particles of the mixture of the deep-sea water concentrate and the skincare gel mixed uniformly does not change in short time interval, so it is appropriate to apply the mixture to human skin immediately.

Figure 6B:
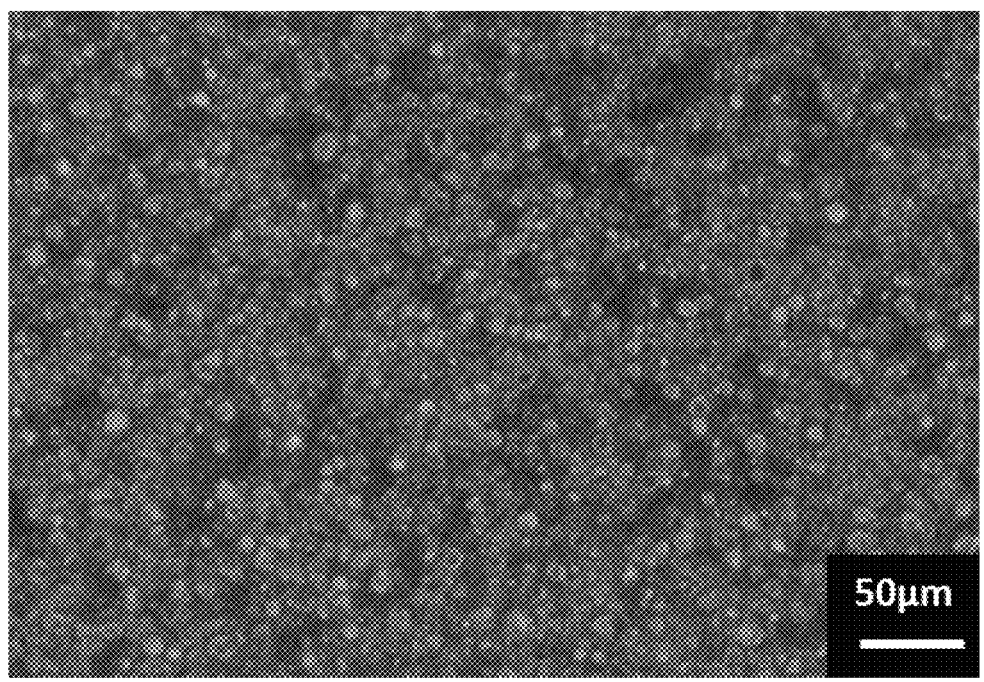
Figure 6C:
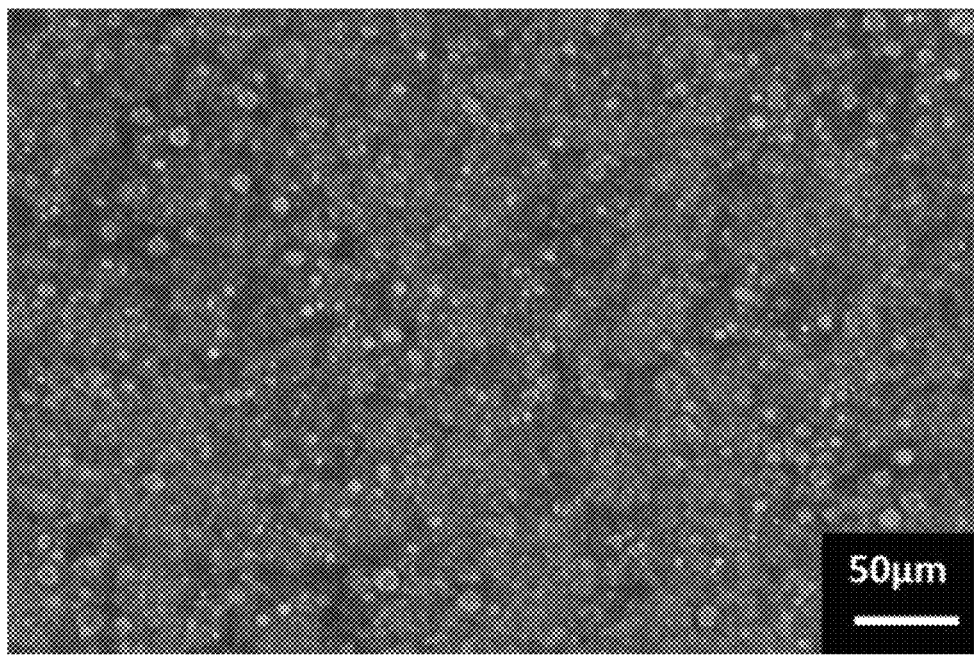
Figure 6D:
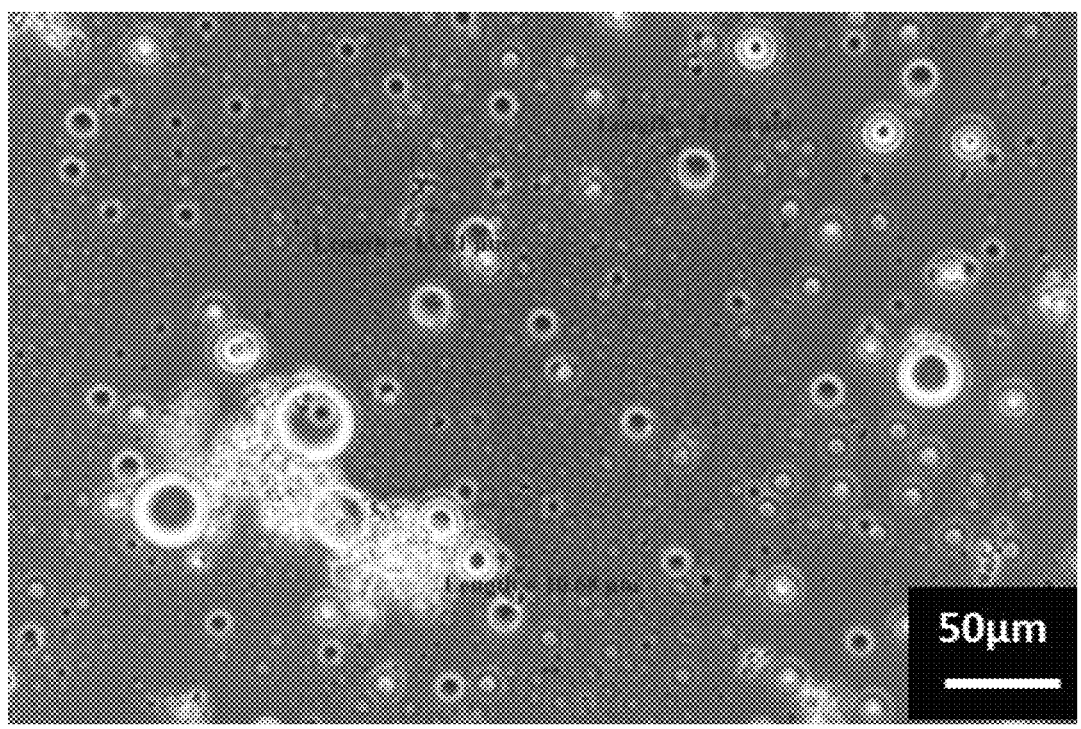

Furthermore, 200× optical microscope is used to observe the difference between microparticles of single dose of skincare gel (as shown in FIG. 6B), a mixture of pure water and skincare gel mixed immediately with a weight ratio of 1:1 (as shown in FIG. 6C), and a mixture of deep-sea water concentrate and skincare gel mixed immediately with a weight ratio of 1:1 (as shown in FIG. 6D).

According to the observation of optical microscope, the cream body of the single-dose of skincare gel (as shown in FIG. 6B), and the cream body of the mixture of pure water and skincare gel mixed immediately with the weight ratio of 1:1 (as shown in FIG. 6C) cannot scatter uniformly to effectively form microparticles, so obvious clustering phenomenon occurs. Otherwise, in the mixture of the deep-sea water concentrate and the skincare gel mixed immediately with a weight ratio of 1:1, it observes that the cream body of skincare gel occurs phase transfer immediately and microparticles form with an average particle size of about 5.035 m. Compared with the 15 m to 50 m of particle size of molecular group of general skincare product, the size of the microparticles of the mixture is reduced one-third to one-tenth, and it is beneficial for improving the probability that molecular groups of the skincare product effectively permeate deep layer of skin.

Embodiment Eight: Measurement of Driving Force of Mixture of Deep-Sea Water Concentrate and Skincare Gel Mixed Immediately The ITRI material and chemical research laboratories are commissioned to perform the experiment. In this experiment, a conductivity analyzer is used to measure conductivity of the mixture of the deep-sea water concentrate and the skincare gel mixed immediately with a weight ratio of 1:1, for explaining the driving force of the mixture of the deep-sea water concentrate and the skincare gel mixed immediately.

The conductivity analyzer is used to measure conductivity of mixtures which are a control group including (a) pure water, and experimental groups including (b) mixture of pure water and skincare gel mixed immediately with a weight ratio of 1:1 and (c) mixture of deep-sea water concentrate and skincare gel mixed immediately with a weight ratio of 1:1. These samples being mixed immediately are measured by the analyzer directly.

TABLE 6

The conductivity test of deep-sea water concentrate liquid and different mixture

| Measure sample | (a) pure water | (b) mixture of pure water and skincare gel mixed immediately with a weight ratio of 1:1 | (c) mixture of deep-sea water concentrate and the skincare gel mixed immediately with a weight ratio of 1:1 |
| --- | --- | --- | --- |
| Conductivity (mS/cm) | 0.008 | 4.18 | 98 |

According to the conductivity test result, the conductivity of the experimental group (c) using the mixture of the deep-sea water concentrate and the skincare gel mixed immediately with the weight ratio of 1:1 is higher than the conductivity of the experimental group (b) using the mixture of the pure water and the skincare gel mixed immediately with a ratio of 1:1, by more than 20 times, and also higher than that of the control group (a) using pure water by even 12,250 times, and the obvious difference in conductivities indicates that the mixture of the deep-sea water concentrate and the skincare gel mixed immediately with a weight ratio of 1:1 can provide good driving force for the mixture, and the driving force can improve permeability of skincare product into the deep layer of skin for effective adsorption, thereby improving effect of the skincare formula.

The present invention disclosed herein has been described by means of specific embodiments. However, numerous modifications, variations and enhancements can be made thereto by those skilled in the art without departing from the spirit and scope of the disclosure set forth in the claims.

What is claimed is:

1. A method of improving a permeability of a skincare formula, consisting of:
   (a) providing a skincare formula and a deep-sea water concentrate, wherein the deep-sea water concentrate comprises magnesium, sodium, potassium, and calcium minerals;
   (b) mixing the skincare formula and the deep-sea water concentrate upon application to induce phase transfer of the skincare formula immediately after the mixing, so as to enhance the permeability of the skincare formula to reach to a depth of skin,
   wherein a concentration of the deep-sea water concentrate is in a range from 80,000 mg/L to 420,000 mg/L, wherein a concentration of magnesium of the deep-sea water concentrate is in a range from 6,500 mg/L to 110,000 mg/L, wherein a concentration of sodium of the deep-sea water concentrate is in a range from 3,800 mg/L to 30,000 mg/L, a concentration of potassium is in a range from 400 mg/L to 18,000 mg/L, and a concentration of calcium is in a range from 100 mg/L to 500 mg/L, wherein the deep-sea water concentrate has a conductivity greater than 4.18 mS/cm, and after the deep-sea water concentrate and the skincare formula are mixed, the mixture is applied to the skin immediately.

2. The method according to claim 1, wherein the deep-sea water concentrate has a salinity in a range from 380 per thousandth to 430 per thousandth.

3. The method according to claim 1, wherein the deep-sea water concentrate is liquid or powder.

4. The method according to claim 1, wherein the skincare formula is in the form of gel or cream.

5. The method according to claim 1, wherein after the deep-sea water concentrate is mixed with the skincare formula, an effective concentration of the deep-sea water concentrate is at least higher than or equal to 1.25 (v/v) %.

* * * * *